US008628471B2

(12) United States Patent
Mazar et al.

(10) Patent No.: US 8,628,471 B2
(45) Date of Patent: Jan. 14, 2014

(54) SYSTEM AND METHOD FOR PREDICTING PATIENT HEALTH WITHIN A PATIENT MANAGEMENT SYSTEM (75) Inventors: Scott T. Mazar, Woodbury, MN (US); Richard Fogoros, Pittsburg, PA (US); Yatheendhar D. Manicka, Woodbury, MN (US); Bruce H. KenKnight, Maple Grove, MN (US); Michael J. Pederson, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 413 days.

(21) Appl. No.: 12/827,985

(22) Filed: Jun. 30, 2010

(65) Prior Publication Data

US 2010/0268095 A1 Oct. 21, 2010

Related U.S. Application Data (63) Continuation of application No. 10/334,283, filed on Jan. 2, 2003, now abandoned.

(51) Int. Cl.
*A61B 5/0452* (2006.01)
*A61B 5/026* (2006.01)
*A61B 5/0205* (2006.01)
*A61B 5/053* (2006.01)

(52) U.S. Cl.
USPC ........... 600/301; 600/506; 600/510; 600/513; 600/547; 607/18; 607/20

(58) Field of Classification Search
USPC ............... 600/506, 510–513, 547; 607/18, 20
See application file for complete search history.

(56) References Cited

U.S. PATENT DOCUMENTS 4,706,689 A  11/1987  Man
4,750,494 A  6/1988  King
5,040,533 A * 8/1991  Fearnot ........................... 607/22
5,116,759 A  5/1992  Klainer et al.
5,331,966 A  7/1994  Bennett et al.
5,629,678 A  5/1997  Gargano et al.
5,876,353 A  3/1999  Riff
6,104,949 A * 8/2000  Pitts Crick et al. ........... 600/547
6,221,011 B1  4/2001  Bardy
6,398,728 B1  6/2002  Bardy (Continued)

FOREIGN PATENT DOCUMENTS

JP  09098964  4/1997

OTHER PUBLICATIONS

"U.S. Appl. No. 10/334,283, Non-Final Office Action mailed Jan. 27, 2009", 20 pgs.
"U.S. Appl. No. 10/334,283, Final Office Action mailed Mar. 31, 2010", 7 pgs.
"U.S. Appl. No. 10/334,283, Non-Final Office Action mailed Oct. 28, 2009", 10 pgs.

(Continued)

*Primary Examiner* — Bill Thomson
*Assistant Examiner* — Shirley Jian
(74) *Attorney, Agent, or Firm* — Schwegman Lundberg & Woessner, P.A.

(57) ABSTRACT

Systems and Methods for predicting patient health and patient relative well-being within a patient management system are disclosed. A preferred embodiment utilizes an implantable medical device comprising an analysis component and a sensing component further comprising a three-dimensional accelerometer, a transthoracic impedance sensor, a cardio-activity sensor, an oxygen saturation sensor and a blood glucose sensor. Some embodiments of a system disclosed herein also can be configured as an Advanced Patient Management System that helps better monitor, predict and manage chronic diseases.

20 Claims, 8 Drawing Sheets

(56) References Cited

U.S. PATENT DOCUMENTS

| | | | |
|---|---|---|---|
| 6,409,675 B1 * | 6/2002 | Turcott | 600/508 |
| 6,459,929 B1 * | 10/2002 | Hopper et al. | 600/513 |
| 6,473,640 B1 * | 10/2002 | Erlebacher | 600/547 |
| 6,512,949 B1 | 1/2003 | Combs et al. | |
| 6,595,927 B2 * | 7/2003 | Pitts-Crick et al. | 600/529 |
| 6,997,879 B1 | 2/2006 | Turcott | |
| 7,226,422 B2 * | 6/2007 | Hatlestsad et al. | 600/534 |
| 7,313,434 B2 * | 12/2007 | Belalcazar et al. | 600/547 |
| 2004/0140209 A1 | 7/2004 | Choi et al. | |

OTHER PUBLICATIONS

"U.S. Appl. No. 10/334,283, Response filed Jan. 5, 2010 to Non Final Office Action mailed Oct. 28, 2009", 12 pgs.

"U.S. Appl. No. 10/334,283, Response filed May 27, 2009 to Non Final Office Action mailed Jan. 27, 2009", 12 pgs.

"Minaturized, Implantable Identification Technology", *VeriChip Corporation*, http://www.adsx.com/prodservpart/verichip.html, (Feb. 5, 2003), 3.

Appell, D, "Getting under your Skin", *Scientific American*, (Jan. 2003), 2.

* cited by examiner

SYSTEM AND METHOD FOR PREDICTING PATIENT HEALTH WITHIN A PATIENT MANAGEMENT SYSTEM

CROSS-REFERENCE TO RELATED APPLICATIONS

This application is a continuation of U.S. application Ser. No. 10/334,283, filed on Jan. 2, 2003, the benefit of priority of which is claimed herein, and which is incorporated herein by reference in its entirety.

TECHNICAL FIELD

The present system relates generally to a Patient Management System and particularly, but not by way of limitation, to such a system that can determine patient health, relative well-being and predictive degradation by using the sensing functions of an implantable medical device and analyzing the sensed patient data to predict patient health.

BACKGROUND

Implantable medical devices are becoming increasingly versatile and able to perform many different physiological sensing functions that enable a clinician to quickly and accurately assess patient health. Traditionally, an accurate assessment of patient health required the clinician to synthesize often divergent or seemingly unrelated indications of patient health. For example, a diagnosis of congestive heart failure might include not only an assessment and evaluation of cardiac function data, but also an evaluation of other physiological factors like patient fatigue or respiration data.

Typically, a clinician will assess patient health by inquiring how the patient feels or asking about the patient's activities and then make an indirect assessment based on the patient's response and the clinician's observation of the patient's appearance. However, these measures are very subjective and are limited to the time of the patient/clinician interaction and the quality of patient recall or willingness to divulge information. These factors affect the quality of the assessment.

Modern implantable medical devices offer objective data to help the clinician assess patient health. Modern medical devices can sense and analyze physiological factors with improved accuracy and report that sensed and analyzed information to the clinician or the patient. The data or information that a medical device reports in the form of a sensed physiological parameter can be characterized as either derived or non-derived data. Non-derived data can be understood as raw biometric information sensed by the medical device that has not been processed to any meaningful degree. For example, non-derived biometric information may comprise the quantified measurement of a patient's heart rate or blood pressure. In contrast, derived data is biometric information that has been analyzed and perhaps assigned some qualitative or quantitative value. For example, as a medical device senses a patient's cardiac cycle and clinically analyzes that information, the medical device may report that an arrhythmia has occurred as the result of sensing and analyzing a cardiac rhythm outside expected parameters. Other derived sensors may include, the cumulative calories burned by daily activity, a weight loss monitor, a participation in activities monitor, a depression monitor or determining the onset of cancer, all of which may be ascertained by sensing physiological data and analyzing that data by using clinically derived algorithms or other analytical tools.

An example of a sensor component of a medical device is an accelerometer. An accelerometer is essentially a device capable of measuring an object's relative orientation in a gravity field. It can directly sense patient movement (non-derived data) and present that information for analysis and perform as a derived sensor. Such derived information might include whether a patient is fatigued by reason of illness or because of overexertion. Thus, relative activity may correspond to relative patient health. In addition to simply determining whether a patient is ambulatory, a sensitive or finely-tuned accelerometer can also determine a patient's relative position, i.e., whether the patient is sitting, standing, sleeping or distinguish whether the patient is prone because he decided to lie down instead of abruptly falling down. A sensitive accelerometer can also detect fine body movement, like the physical reflexes of a person coughing or sneezing.

Coughing is often more than an indication of a respiratory irritation or condition like asthma or the onset of the common cold, but may also be a common side effect of certain drugs. For example, Angiotensin Converting Enzyme ("ACE") inhibitors may cause a patient to cough when the patient's dosage is too high. Thus, coughing may be used to titrate the appropriate dose of a drug like an ACE inhibitor.

Implantable medical devices comprising cardio-sensors, i.e., pacemakers, can also monitor and sense a patient's cardiac activity and provide remedial therapy. In addition, such medical devices can sense and measure transthoracic impedance as a means to evaluate patient respiration data.

As a measurement of respiration, modern implantable medical devices often employ a sensor that measures transthoracic impedance. Transthoracic impedance is essentially the measure of a voltage across some known spacing or distance. To measure this voltage, the medical device drives a current from the device to the tip of a lead and voltage is measured from another area proximate to the device and another area proximate to the lead. For example, as a person's heart pumps, the transthoracic impedance changes because the heart is moving relative to the implanted device. Similarly, as a person's lung inflates and deflates as he breathes, the geometry of the current flowing between the device and the tip of the lead changes. In measuring respiration, the spacing or distance is situated in such a way that the distance crosses over either a person's left or right lung. Thus, when the geometry changes, the resistance also changes. In the context of breathing, the periodicity of the resistance also can serve as an indication of the relative depth or shallowness of breathing. In other words, a transthoracic impedance sensor can determine the symmetrical relationship between inhalation and exhalation. The symmetry of inhalation to exhalation can establish a pattern of respiration that may have clinical meaning, like determining asthma, apnea or chronic obstructive pulmonary disease ("COPD"). Within the context of detecting an asthma attack, a symmetrical breathing pattern recognized by a transthoracic impedance monitor may comprise the forced expiratory volume over one second ("FEV1"). Modern medical devices that measure transthoracic impedance can be configured to filter out the cardiac component and other impedance noise and concentrate on measuring the breathing component.

An implantable medical device may also employ a sensor that measures blood glucose levels. In this way, the medical device may predict the need for insulin therapy before the patient or clinician observes acute symptoms of hyperglycemia.

However, the data sensed by modern implantable medical devices is often presented in a form that merely reduces the data to some numerical or relative value that requires the clinician to further analyze the numerical or relative value output to make a meaningful clinical assessment. In addition, current implantable medical devices frequently are not analytically robust enough to provide meaningful diagnostic assessments or predictions of patient health beyond the mere reporting of physiological data. Merely reporting physiological data can be of limited value due to a person's natural ability to initially compensate for nascent changes in health status. Because of such analytical and perceptual limitations, sensing cardiac activity or transthoracic impedance data through a single implantable medical device may only provide the clinician with a useful starting point for further clinical analysis.

Thus, for these and other reasons, there is a need for a Patient Management System comprising an implantable medical device further comprising various physiological sensors that sense and report patient data. The system is further adapted to analyze the sensed data in a manner that yields an accurate assessment or prediction of patient health or relative well-being. In this way, the system can be configured to not only report a relative state of patient health and detect early stage disease progression, but also alert the clinician to patient health degradation before the onset of an acute episode or symptomatic illness.

SUMMARY

According to one aspect of the invention, there is provided a system and method for predicting patient health and relative well-being within a Patient Management System using an implantable medical device configured with multiple physiological sensors in communication with other components of the system via a communications network. The Patient Management System further includes an analytical component contained within the medical device or outside the device or a combination of internal and external analytical components. A non-limiting example of such an analytical component is an externally-based Advanced Patient Management System. As used herein, "physiological function data," "physiology data," "patient data" and "patient health data" are substantively synonymous terms and relate to a measurable or relative physiological parameter. In addition to physical parameters like heart rate, respiration and blood chemistry, physiological parameters may include, for example, subjective evaluations of well-being, perceived emotional state and other psychological attributes. Also, as used herein, a "clinician" can be a physician, physician assistant (PA), nurse, medical technologist, or any other patient health care provider.

In one embodiment of a system for predicting patient health and relative well-being within a patient management system, the system comprises a medical device further comprising a sensing component, an analysis component and a communications component. The sensing component includes one or more base sensors adapted to sense physiological function data. The analysis component is adapted to analyze physiological data sensed by the sensing component and detect subtle, early indications of changes in disease state. The communications component is adapted to communicate sensed and analyzed physiological data to the components of the system.

In another embodiment of the system for predicting patient health and relative well-being within a patient management system, the medical device comprising sensing, analysis and communications components is implanted within a patient, and the sensing component includes an accelerometer. The accelerometer can be configured to detect a patient's fine and gross body motion, and can be a one-, two- or three-dimensional accelerometer. Example analysis includes detecting changes in measured accelerometer patterns that are indicative of early occurrence of a new disease state or onset of illness or indicate progression of a disease.

In a further embodiment of the system for predicting patient health and relative well-being within a patient management system, the sensing component of the implantable medical device comprises an accelerometer and a transthoracic impedance sensor. In this embodiment, the implantable medical device is adapted to detect a patient's fine and gross body motion and respiration parameters. Example analysis includes detecting changes in transthoracic impedance variation patterns that are indicative of early occurrence of a new disease state (such as COPD) or onset of illness (such as asthma) or indicate progression of a disease (such as DC impedance indicating lung fluid accumulation which corresponds to progression of heart failure). Further, the sensed data can be used in combination to cross-validate sensed conclusions, such as a change in accelerometer data pattern coincident with inhalation/exhalation time ratio measured by transthoracic impedance to indicate progression of asthma.

In yet another embodiment of the system for predicting patient health and relative well-being within a patient management system, the sensing component of the implantable medical device comprises an accelerometer, a transthoracic impedance sensor and a cardio-activity sensor. In this embodiment, the implantable medical device is adapted to detect a patient's fine and gross body motion, respiration parameters, and cardiac-activity parameters. Example analysis includes monitoring left and right intracardial R-wave amplitude and either singly reporting changes or correlating changes with changes in accelerometer and transthoracic impedance to form an early and confident indication of onset of pulmonary edema.

In yet a further embodiment of the system for predicting patient health and relative well-being within a patient management system, the sensing component of the implantable medical device comprises an accelerometer, a transthoracic impedance sensor, and an oxygen saturation sensor. In this embodiment, the implantable medical device is adapted to detect a patient's fine and gross body motion, respiration parameters, cardiac-activity parameters and blood gas data. Example analysis includes combining changes in accelerometer and transthoracic impedance with blood oxygen saturation to form an early and confident indication of onset or progression of pulmonary edema.

In a preferred embodiment of the system for predicting patient health and relative well-being within a patient management system, the sensing component of the implantable medical device comprises a three-dimensional accelerometer, a transthoracic impedance sensor, a cardio-activity sensor, an oxygen saturation sensor and a blood glucose sensor. In this embodiment, the implantable medical device is adapted to detect a patient's fine and gross body motion, respiration parameters, cardiac-activity parameters, blood gas data and episodes of hyper- and hypoglycemia. Example analysis includes combining changes in accelerometer data, transthoracic impedance, blood oxygen saturation, cardio-activity and blood glucose for an early and confident indication of onset and changes in cardiac and pulmonary disease states.

By selecting other base sensors, early and confident indications of onset or progression of diseases beyond cardiopulmonary can be made. By way of non-limiting example only, other base sensors might include a cardiac output/ejection fraction sensor; a chamber pressure sensor; a temperature sensor; sodium, potassium, calcium and magnesium sensors; a pH sensor; a partial oxygen sensor; a partial CO2 sensor; a cholesterol and triglyceride sensor; a catecholamine sensor; a creatine phosphokinase sensor; a lactate dehydrogenase sensor; a troponin sensor; a prothrombin time sensor; a complete blood count sensor; a blood urea nitrogen sensor; a body weight sensor; a blood (systemic) pressure sensor; a adrenocorticotropic hormone sensor; a thyroid marker sensor; a gastric marker sensor and a creatinine sensor. Data from these sensors can be analyzed to predict or detect, by way of non-limiting example only, the early onset of stroke, pain quantification/determination, chronic depression, cancer tissue (onset, progression, recurrence), syncope, autonomic tone, myocardial infarct, ischemia and seizure.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which are shown by way of illustration, specific embodiments or examples. These embodiments may be combined, other embodiments may be utilized, and structural, logical and electrical changes may be made without departing from the spirit and scope of the present invention. The following detailed description is, therefore, not to be taken in a limiting sense, and the scope of the present invention is defined by the appended claims and their equivalents.

The present system and method are described with respect to an implantable medical device as a component of a Patient Management System capable of predicting patient health and relative well-being by the comprehensively analyzing sensed physiological data.

Figure 1:
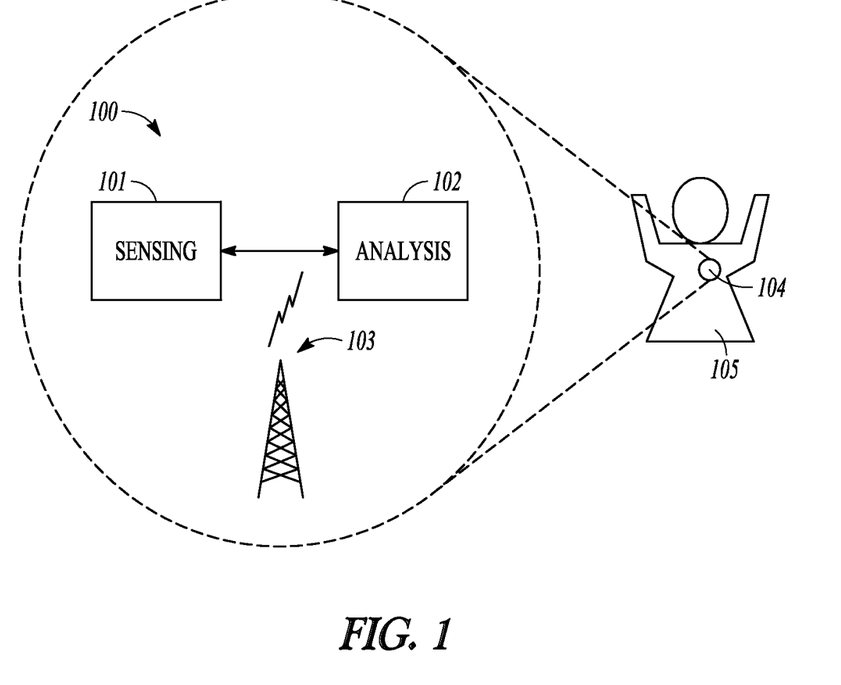
FIG. 1 is a schematic/block diagram illustrating generally, among other things, one embodiment of the system and method for predicting patient health within a patient management system.

FIG. 1 is a schematic/block diagram illustrating generally an embodiment of the system and method for predicting patient health and relative well-being within a patient management system 100. The system comprises a medical device further comprising a sensing component 101, an analysis component 102 and a communications component 103. The medical device can be implantable 104 within a patient 105.

The sensing component 101 includes one or more sensors adapted to sense physiological data. The sensors may comprise an accelerometer, a transthoracic impedance sensor, an oxygen saturation sensor, and a cardio-activity sensor.

The analysis component 102 is adapted to analyze physiological data sensed by the sensing component. Analysis may be internal and/or external to the patient. Analysis may include the use of clinically derived algorithms to analyze the biometric data in a way that yields a clinically relevant output. The algorithms can be the result of the extraction, codification and use of collected expert knowledge for the analysis or diagnosis of medical conditions. For example, the algorithms can comprise institutional analytical or diagnostic techniques used in specific clinical settings. By reducing the analytical or diagnostic methodologies of institutions like the Cleveland Clinic, the Mayo Clinic or the Kaiser Permanente system to algorithmic expression, a patient will enjoy the benefit of the medical expertise of a leading medical institution without having to visit the institution. The analysis and sensing components are further adapted to electronically communicate with the communications component.

The communications component 103 is adapted to communicate sensed and analyzed physiological data to the components of the system, whether the components are internal or external to the patient.

Figure 2:
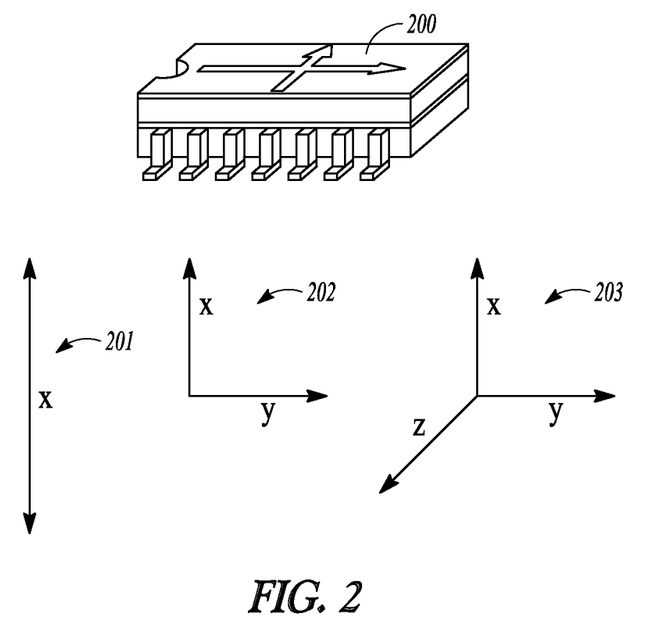
FIG. 2 is a schematic/block diagram illustrating generally, among other things, another embodiment of the system and method for predicting patient health within a patient management system comprising an accelerometer.

FIG. 2 is a schematic/block diagram illustrating generally an embodiment of the accelerometer 200 component of the system and method for predicting patient health and relative well-being within a patient management system. The accelerometer 200 can be configured to detect a patient's fine and gross body motion. A suitable accelerometer includes a one-dimensional, two-dimensional 200 or three-dimensional accelerometer. Typically, a one-dimensional accelerometer only measures movement along a single axis 201 as further illustrated in FIG. 2. A two-dimensional accelerometer typically measures movement along two orthogonal axes 202. A three-dimensional accelerometer measures movement along three orthogonal axes 203. When the system comprises a three-dimensional accelerometer, the system can determine person's body position with greatest accuracy. Thus, in addition to detecting gross body movement, a sensitive accelerometer may be adapted to detect fine body movement, like a person coughing. When the system is configured to analyze accelerometer data to determine whether a person is coughing, a clinician can utilize that derivative information two assist in determining the onset of a common cold, influenza or the proper dosage of a drug, like an ACE inhibitor, that may cause a coughing side effect when the dosage is too high. In addition, coughing or other activity sensed by the accelerometer 200 may be used to titrate the dosage of other drugs as a component of a near-term drug delivery system, wherein the titration analysis is communicated to the patient or the clinician.

Figure 3:
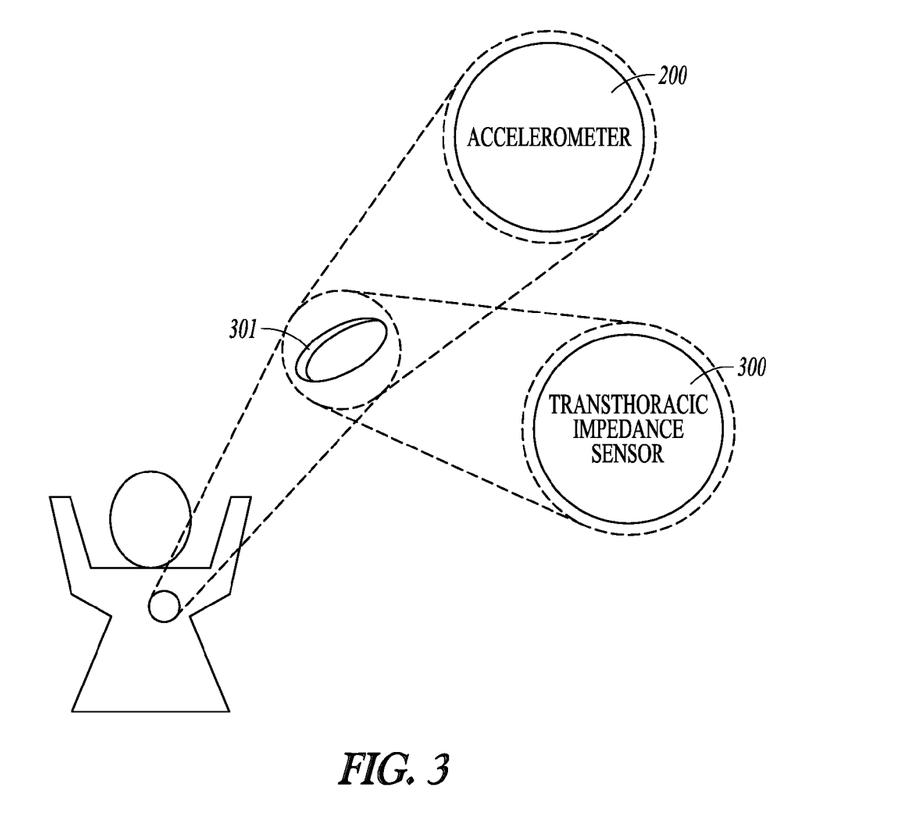
FIG. 3 is a schematic/block diagram illustrating generally, among other things, another embodiment of the system and method for predicting patient health within a patient management system comprising an accelerometer and a transthoracic impedance sensor.

FIG. 3 is a schematic/block diagram illustrating generally an embodiment of the transthoracic impedance sensor 300 component of the system and method for predicting patient health and relative well-being within a patient management system. In one embodiment, as illustrated in FIG. 3, the transthoracic impedance sensor 300 is a component of an implantable medical device 301. In this embodiment, the implantable medical device comprises an accelerometer 200 as illustrated in FIG. 2 and a transthoracic impedance sensor 300. A transthoracic impedance sensor 300 may be adapted to sense impedance changes in the heart or lungs or both. The transthoracic impedance sensor can be configured to filter out the cardiac component and other impedance noise and focus on respiration measurement. In such a filtered embodiment, the transthoracic impedance sensor 300 can assist the clinician in predicting the onset or presence of an asthma attack, apnea, COPD and FEV1. Further, in this embodiment, the transthoracic impedance sensor 300 may also be configured to detect the accumulation of fluid in the lungs. Such detection may also serve to predictively indicate the onset or existence of pulmonary disease.

Figure 4:
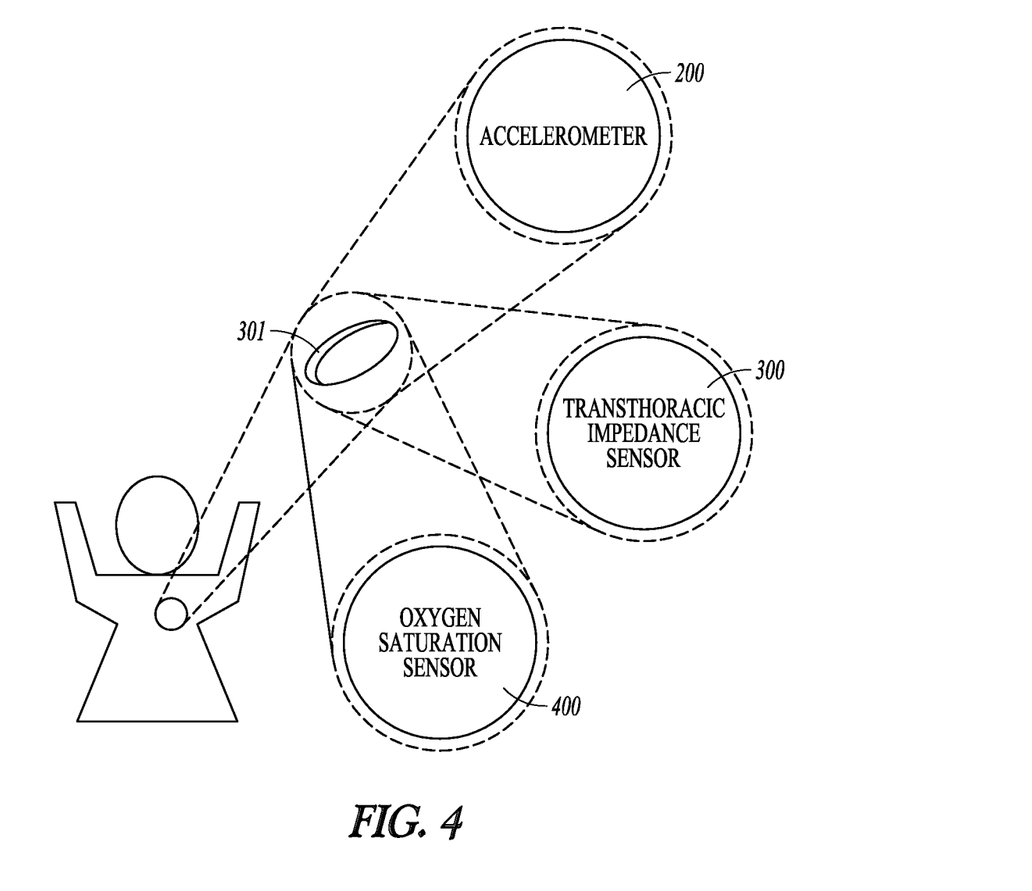
FIG. 4 is a schematic/block diagram illustrating generally, among other things, another embodiment of the system and method for predicting patient health within a patient management system comprising an accelerometer, a transthoracic impedance sensor and an oxygen saturation sensor.

FIG. 4 is a schematic/block diagram illustrating generally an embodiment of the oxygen saturation sensor 400 component of the system and method for predicting patient health and relative well-being within a patient management system. In one embodiment, as illustrated in FIG. 4, the oxygen saturation sensor 400 is a component of an implantable medical device 301. In this embodiment, the implantable medical device comprises an accelerometer 200 as illustrated in FIG. 2, a transthoracic impedance sensor 300 and an oxygen saturation sensor 400. An oxygen saturation sensor 400 determines the ratio between the deoxygenated hemoglobin and oxygenated hemoglobin. In a healthy person, breathing air at sea level, the level of saturation is between 96% and 98%. Abnormal levels may indicate a respiratory or environmental problem. When combined with other measurements of patient health, a patient's oxygen saturation level may provide further evidence of patient health or relative well-being.

Figure 5:
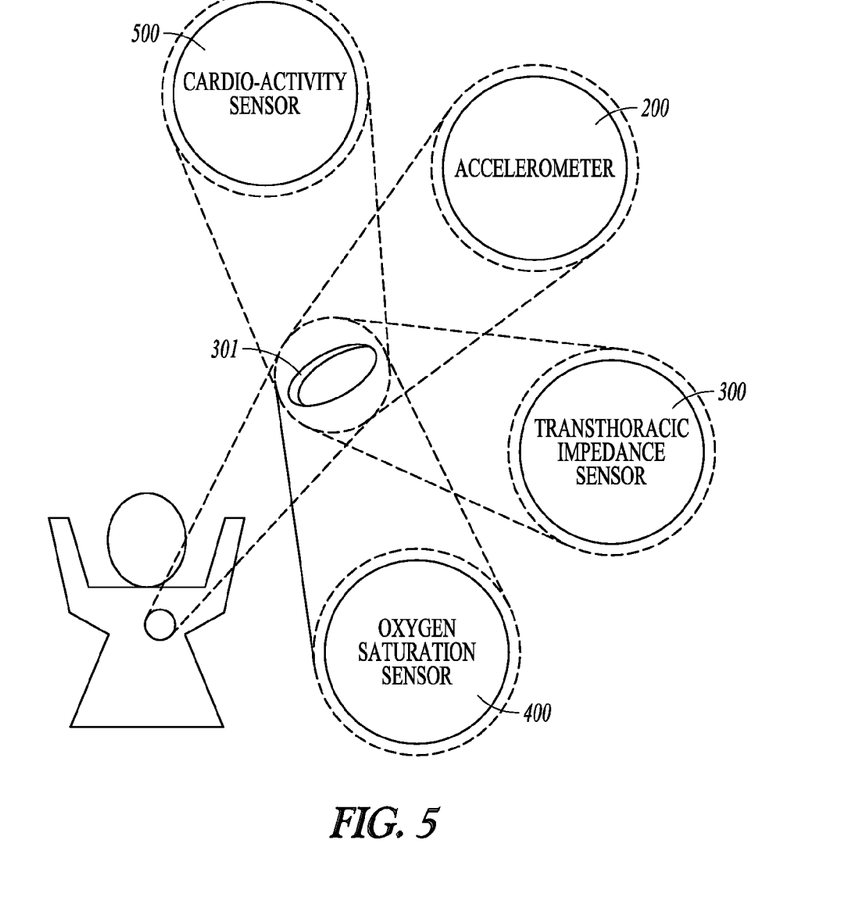
FIG. 5 is a schematic/block diagram illustrating generally, among other things, another embodiment of the system and method for predicting patient health within a patient management system comprising an accelerometer, a transthoracic impedance sensor, an oxygen saturation sensor and a cardio-activity sensor.

FIG. 5 is a schematic/block diagram illustrating generally an embodiment of the cardio-activity sensor 500 component of the system and method for predicting patient health and relative well-being within a patient management system. In one embodiment, as illustrated in FIG. 5, the cardio-activity sensor 500 is a component of an implantable medical device 301. In this embodiment, the implantable medical device comprises an accelerometer 200 as illustrated in FIG. 2, a transthoracic impedance sensor 300, an oxygen saturation sensor 400, and a cardio-activity sensor 500. The cardio-activity sensor 500 may be configured to detect cardiac arrhythmias. Depending on the nature of the arrhythmia, the cardio-activity sensor 500 may cause therapy to be directed to the patient in the form of a low energy electrical stimuli, i.e., pace pulse, or a defibrillation countershock. The cardio-activity sensor 500 may also be used to signal a clinician that an arrhythmia requires further analysis or medical intervention. The cardio-activity sensor 500 in this embodiment may also assist in predicting stroke by measuring ST-segment changes in an electrocardiogram and conveying that information to the analysis component 102 to confirm ST-segment elevations or abnormalities.

Figure 6:
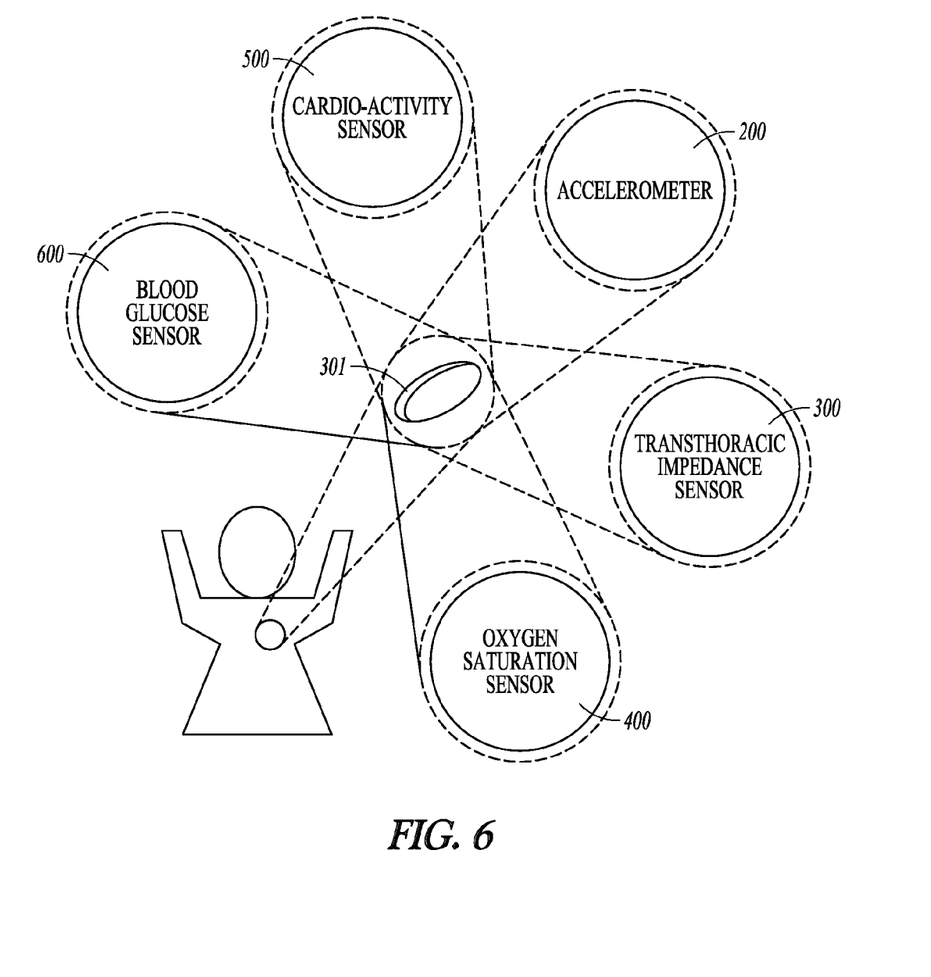
FIG. 6 is a schematic/block diagram illustrating generally, among other things, another embodiment of the system and method for predicting patient health within a patient management system comprising an accelerometer, a transthoracic impedance sensor, an oxygen saturation sensor, a cardio-activity sensor and a blood glucose sensor.

FIG. 6 is a schematic/block diagram illustrating generally an embodiment of the blood glucose sensor 600 component of the system and method for predicting patient health and relative well-being within a patient management system. In one embodiment, as illustrated in FIG. 6, the blood glucose sensor 600 is a component of an implantable medical device 301. In this embodiment, the implantable medical device comprises an accelerometer 200 as illustrated in FIG. 2, a transthoracic impedance sensor 300, an oxygen saturation sensor 400, a cardio-activity sensor 500 and a blood glucose sensor 600. The blood glucose sensor 600 may be configured to detect elevations or de-elevations in blood glucose. Depending on the nature of the blood glucose level, the blood glucose sensor 600 may cause therapy to be directed to the patient in the form of insulin administration or be used to signal an alert to the patient or clinician.

Figure 7:
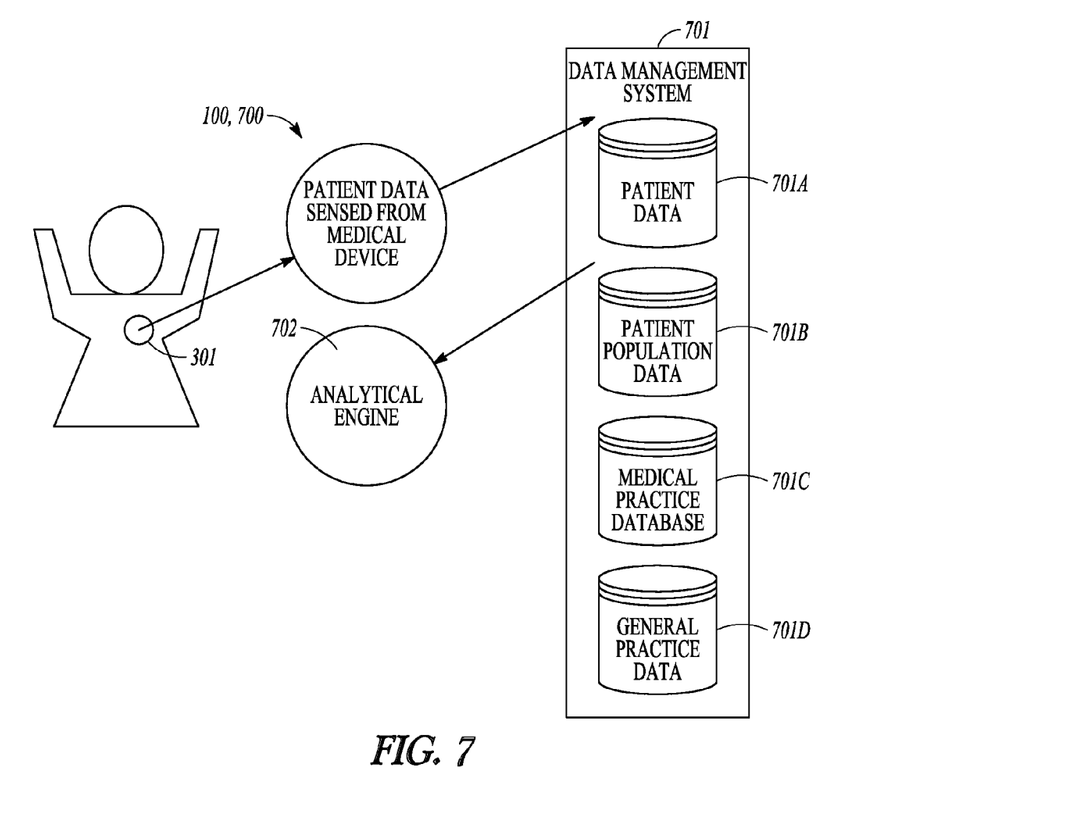
FIG. 7 is a schematic/block diagram illustrating generally, among other things, another embodiment of the system and method for predicting patient health within an Advanced Patient Management system.

FIG. 7 is a schematic/block diagram illustrating generally an embodiment of the system and method for predicting patient health and relative well-being within a patient management system 100 illustrating the analysis of patient data by an externally-based Advanced Patient Management System ("APM") 700.

APM is a system that helps patients, their physicians and their families to better monitor, predict and manage chronic diseases. In the embodiment shown in FIG. 7, the APM system 700 consists of three primary components: 1) an implantable medical device 301 with sensors adapted to monitor physiological data, 2) a Data Management System ("DMS") 701, adapted to process and store patient data 701a collected from the sensors, patient population data 701b, medical practice data 601c further comprising clinically derived algorithms, and general practice data 701d, and 3) an analytical engine 702 adapted to analyze data from the DMS. APM is designed to support physicians and other clinicians in using a variety of different devices, patient-specific and non-specific data, along with medication therapy, to provide the best possible care to patients. Currently, implanted devices often provide only limited sensing, analysis and therapy to patients. APM moves the device from a reactive mode into a predictive one that allows a clinician to use APM to predict patient health.

Figure 8:
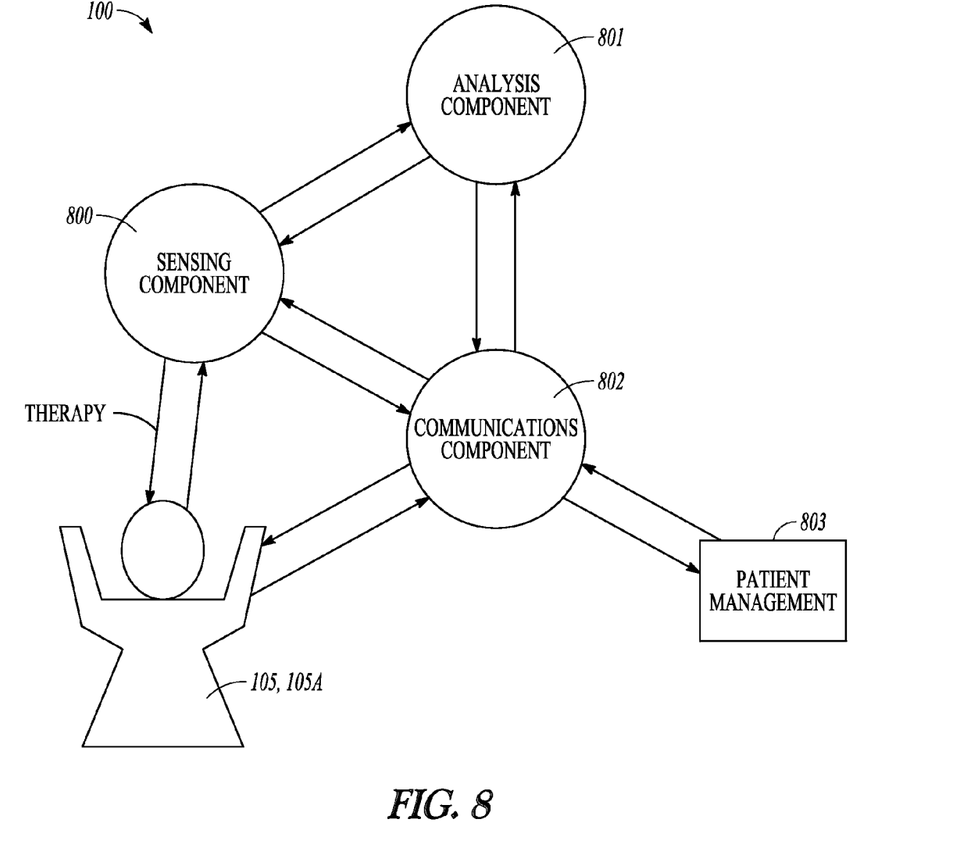
FIG. 8 is a flow diagram illustrating generally, among other things, the interactive functions of the system and method for predicting patient health within a patient management system.

FIG. 8 is a flow diagram illustrating generally the interactive functions of the system and method for predicting patient health and relative well-being within a patient management system 100. As illustrated in FIG. 8, the sensing 800, analysis 701 and communications 802 components are interactive, thus allowing the components to communicate and share data. By way of non-limiting example only, the sensing component 800 would first sense physiological function data from a patient 105. The sensing component 800 may be further adapted to provide therapy to the patient 105. That data would then be transmitted to analysis component 801 for analysis. Analysis may comprise the use of clinically derived algorithms and may be performed internal and/or external to the patient 105. Based on the analysis, the sensing component 800 may be further adapted to provide therapy to the patient 105. The analyzed data is then received by communications module 802, which reports the analyzed data in the form of a determination of patient health or relative well-being to a patient 105 or clinician 105*a*. The communications component 802 may also be in communication with a patient management system, including an externally based Advanced Patient Management system 803. Communication can be in the form of wired or wireless electronic communication.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including," "includes" and "in which" are used as the plain-English equivalents of the respective terms "comprising," "comprises" and "wherein."

What is claimed is:

1. An implantable device comprising:
   an accelerometer to sense body motion data represented as an accelerometer data pattern and;
   an impedance sensor to sense transthoracic impedance data;
   a cardio-activity sensor to sense cardiac data;
   an analysis component; and
   a communications component communicatively coupled to the accelerometer, the impedance sensor, and the cardio-activity sensor, the communications component configured to communicate the body motion data, the transthoracic impedance data, and cardiac data to the analysis component,
   the analysis component configured to:
      obtain a transthoracic impedance variation pattern from the transthoracic impedance data;
      identify a possible illness from the transthoracic impedance variation pattern, with the possible illnesses including an onset of asthma and a progression of heart failure;
      obtain an inhalation/exhalation time ratio measured by the transthoracic impedance data; and
      determine whether the possible illness is likely a progression of heart failure by removing the possibility of the possible illness being asthma based on the inhalation/exhalation time ratio and the accelerometer data pattern.

2. The implantable device of claim 1, wherein the impedance sensor is configured to sense an inhalation/exhalation ratio indicative of a progression of asthma indicated by the inhalation/exhalation time ratio.

3. The implantable device of claim 1, wherein the impedance sensor is configured to sense a variation pattern indicative of an onset of chronic obstructive pulmonary disease indicated by the variation pattern, and wherein the analysis module is configured to determine whether the possible illness is an onset of chronic obstructive pulmonary disease based on the variation pattern, the inhalation/exhalation time ratio, and the accelerometer data pattern.

4. The implantable device of claim 1, wherein the impedance sensor is configured to sense an indication of lung fluid accumulation indicative of a progression of heart failure indicated by the lung fluid accumulation, and wherein the analysis module is configured to determine whether the possible illness is a progression of heart failure based on the lung fluid accumulation, the inhalation/exhalation time ratio, and the accelerometer data pattern.

5. The implantable device of claim 1, wherein the cardio-activity sensor is configured to sense left and right intracardial R-wave amplitudes indicative of an onset of pulmonary edema indicated by the left and right intracardial R-wave amplitudes, and wherein the analysis module is configured to correlate changes in accelerometer and transthoracic impedance to determine whether the possible illness as an onset of pulmonary edema.

6. The implantable device of claim 1, wherein the accelerometer is a multi-axis accelerometer.

7. The implantable device of claim 1, comprising an oxygen saturation sensor to sense blood oxygen saturation and wherein the analysis component is configured to use the blood oxygen saturation to detect an onset or change in a cardiac or pulmonary disease state.

8. The implantable device of claim 1, wherein the analysis component is incorporated into the implantable device.

9. A computer-readable storage medium comprising instructions, which when executed by a machine, cause the machine to:
   receive body motion data from an accelerometer;
   receive transthoracic impedance data from an impedance sensor;
   receive cardiac data from a cardio-activity sensor;
   obtain a transthoracic impedance variation pattern from the transthoracic impedance data;
   identify a possible illness from the transthoracic impedance variation pattern, with the possible illnesses including an onset of asthma, an occurrence of chronic obstructive pulmonary disease, and a progression of heart failure;
   obtain an accelerometer data patter from the body motion data;
   obtain an inhalation/exhalation time ratio measured by the transthoracic impedance data; and
   determine whether the possible illness is likely a progression of heart failure by removing the possibility of the possible illness being asthma based on the inhalation/exhalation time ratio and the accelerometer data pattern.

10. The computer-readable storage medium of claim 9, wherein the transthoracic impedance data includes an inhalation/exhalation time ratio and wherein possible illnesses include a progression of asthma indicated by the inhalation/exhalation time ratio.

11. The computer-readable storage medium of claim 9, wherein the possible illnesses include an onset of chronic obstructive pulmonary disease indicated by the variation pattern, and wherein the instructions include instructions to determine whether the possible illness is an onset of chronic obstructive pulmonary disease based on the variation pattern, the inhalation/exhalation time ratio, and the accelerometer data pattern.

12. The computer-readable storage medium of claim 9, wherein the transthoracic impedance data includes an indication of lung fluid accumulation and wherein the possible illnesses include a progression of heart failure indicated by the lung fluid accumulation, and wherein the instructions include instructions to determine whether the possible illness is a progression of heart failure based on the lung fluid accumulation, the inhalation/exhalation time ratio, and the accelerometer data pattern.

13. The computer-readable storage medium of claim 9, wherein the cardiac data includes left and right intracardial R-wave amplitudes and wherein the possible illnesses include an onset of pulmonary edema indicated by the left and right intracardial R-wave amplitudes, and wherein the instructions include instructions to correlate changes in accelerometer and transthoracic impedance to determine whether the possible illness as an onset of pulmonary edema.

14. The computer-readable storage medium of claim 9, comprising instructions to:
receive blood oxygen saturation from an oxygen saturation sensor; and
use the blood oxygen saturation to detect an onset or change in a cardiac or pulmonary disease state.

15. A method comprising:
receiving body motion data from an accelerometer;
receiving transthoracic impedance data from an impedance sensor;
receiving cardiac data from a cardio-activity sensor;
obtaining a transthoracic impedance variation pattern from the transthoracic impedance data;
identifying a possible illness from the transthoracic impedance variation pattern, with the possible illnesses including an onset of asthma, an occurrence of chronic obstructive pulmonary disease, and a progression of heart failure;
obtaining an accelerometer data patter from the body motion data;
obtaining an inhalation/exhalation time ratio measured by the transthoracic impedance data; and
determining whether the possible illness is likely a progression of heart failure by removing the possibility of the possible illness being asthma based on the inhalation/exhalation time ratio and the accelerometer data pattern.

16. The method of claim 15, wherein the transthoracic impedance data includes an inhalation/exhalation time ratio and wherein the possible illnesses include a progression of asthma indicated by the inhalation/exhalation time ratio.

17. The method of claim 15, wherein the possible illnesses include an onset of chronic obstructive pulmonary disease indicated by the variation pattern, and wherein the method includes determining whether the possible illness is an onset of chronic obstructive pulmonary disease based on the variation pattern, the inhalation/exhalation time ratio, and the accelerometer data pattern.

18. The method of claim 15, wherein the transthoracic impedance data includes an indication of lung fluid accumulation and wherein the possible illnesses include a progression of heart failure indicated by the lung fluid accumulation, and wherein the method includes determining whether the possible illness is a progression of heart failure based on the lung fluid accumulation, the inhalation/exhalation time ratio, and the accelerometer data pattern.

19. The method of claim 15, wherein the cardiac data includes left and right intracardial R-wave amplitudes and wherein the possible illnesses include an onset of pulmonary edema indicated by the left and right intracardial R-wave amplitudes, and wherein the method includes correlating changes in accelerometer and transthoracic impedance to determine whether the possible illness as an onset of pulmonary edema.

20. The method of claim 15, comprising:
receiving blood oxygen saturation from an oxygen saturation sensor; and
using the blood oxygen saturation to detect an onset or change in a cardiac or pulmonary disease state.

* * * * *